United States Patent
Scheiner et al.

[19]

[11] Patent Number: 6,152,954
[45] Date of Patent: Nov. 28, 2000

[54] SINGLE PASS LEAD HAVING RETRACTABLE, ACTIVELY ATTACHED ELECTRODE FOR PACING AND SENSING

[75] Inventors: Avram Scheiner, Vadnais Heights; Ronald W. Heil, Jr., Roseville; Qingsheng Zhu, Little Canada; Peter T. Kelley, Buffalo; David M. Flynn, Lino Lakes; John E. Heil, North Oaks, all of Minn.

[73] Assignee: Cardiac Pacemakers, Inc., St. Paul, Minn.

[21] Appl. No.: 09/121,006

[22] Filed: Jul. 22, 1998

[51] Int. Cl.[7] .................................................. A61N 1/05
[52] U.S. Cl. ................................................................ 607/123
[58] Field of Search ................................. 600/373–375, 600/381; 607/122–128

[56] References Cited

U.S. PATENT DOCUMENTS

| | | | |
|---|---|---|---|
| 3,614,955 | 10/1971 | Mirowski | 128/419 D |
| 3,804,098 | 4/1974 | Friedman | 128/404 |
| 3,835,845 | 9/1974 | Maher | 128/64 |
| 3,942,536 | 3/1976 | Mirowski et al. | 128/419 D |
| 3,949,757 | 4/1976 | Sabel | 128/404 |

(List continued on next page.)

FOREIGN PATENT DOCUMENTS

| | | | |
|---|---|---|---|
| 0057877 | 8/1982 | European Pat. Off. | 607/121 |
| 0211166 | 2/1987 | European Pat. Off. | A61N 1/05 |
| 0452278 | 10/1991 | European Pat. Off. | A61N 1/05 |
| 0460324 | 12/1991 | European Pat. Off. | A61N 1/05 |
| 0573275 | 12/1993 | European Pat. Off. . | |
| 0612538 | 8/1994 | European Pat. Off. | A61N 1/05 |
| 0620024 | 10/1994 | European Pat. Off. . | |
| 0672431 | 9/1995 | European Pat. Off. | A61N 1/05 |
| 0709111 | 5/1996 | European Pat. Off. . | |
| 0813886 | 12/1997 | European Pat. Off. . | |
| 2588758 | 4/1987 | France | A61N 1/05 |
| 2827595 | 5/1978 | Germany . | |
| 2949782A1 | 6/1981 | Germany . | |
| 3-168161 | 7/1991 | Japan . | |
| 4-40966 | 2/1992 | Japan . | |
| 2032278 | 6/1980 | United Kingdom | A61M 25/00 |
| 2240721 | 8/1991 | United Kingdom . | |
| 89/06148 | 7/1989 | WIPO | A61N 1/05 |
| 92/07616 | 5/1992 | WIPO . | |
| WO95/08365 | 3/1995 | WIPO . | |

OTHER PUBLICATIONS

Fain, et al., "A New Internal Defibrillation Lead System: Intrapericardial Placement Without Thoracotomy", *Abstracts Circulation*, 76, Suppl. IV, 1839 (Oct. 1987).

(List continued on next page.)

*Primary Examiner*—Jeffrey R. Jastrzab
*Attorney, Agent, or Firm*—Schwegman, Lundberg, Woessner & Kluth, P.A.

[57] ABSTRACT

A single-pass endocardial lead electrode adapted for implantation on or about the heart and for connection to a system for monitoring or stimulating cardiac activity including a lead body with a circumferential outer surface. The lead includes a first distal end electrode which has a first electrical conducting surface which is for positioning within the ventricle of the heart. The lead body also has a second electrode which has a second electrical conducting surface adapted for positioning within the atrium of the heart. Both of the first and the second electrodes are adapted for positioning and fixation to the wall. An active fixation element is used as part of the second electrode. The lead body also includes a curved portion which facilitates the positioning and fixing of the second electrode. In another embodiment, the main lead body includes a recess into which an atrial lead body and the active fixation element attached to one end can travel from a recessed position to a position for fixation to the wall of the heart. The active fixation element which can also be moved by turning the terminal pin.

30 Claims, 4 Drawing Sheets

U.S. PATENT DOCUMENTS

| | | | |
|---|---|---|---|
| 4,013,081 | 3/1977 | Kolenik | 128/419 |
| 4,030,508 | 6/1977 | Thalen | 128/418 |
| 4,030,509 | 6/1977 | Heilman et al. | 124/419 D |
| 4,057,067 | 11/1977 | Lajos | 128/418 |
| 4,106,512 | 8/1978 | Bisping | 128/418 |
| 4,136,703 | 1/1979 | Wittkampf | 128/419 P |
| 4,154,247 | 5/1979 | O'Neill | 128/419 P |
| 4,217,913 | 8/1980 | Dutcher | 128/785 |
| 4,235,246 | 11/1980 | Weiss | 128/758 |
| 4,270,549 | 6/1981 | Heilman | 128/784 |
| 4,291,707 | 9/1981 | Heilman et al. | 128/784 |
| 4,299,239 | 11/1981 | Weiss et al. | 128/785 |
| 4,311,153 | 1/1982 | Smits | 128/785 |
| 4,326,534 | 4/1982 | Axelgaard et al. | 128/421 |
| 4,393,883 | 7/1983 | Smyth et al. | 607/123 |
| 4,402,329 | 9/1983 | Williams | 607/122 |
| 4,458,677 | 7/1984 | McCorkle, Jr. | 607/122 |
| 4,463,765 | 8/1984 | Gold | 128/785 |
| 4,497,326 | 2/1985 | Curry | 128/785 |
| 4,532,931 | 8/1985 | Mills | 128/419 |
| 4,548,203 | 10/1985 | Tacker, Jr. et al. | 128/419 |
| 4,553,548 | 11/1985 | Varrichio et al. | 128/421 |
| 4,559,951 | 12/1985 | Dahl et al. | 128/642 |
| 4,567,900 | 2/1986 | Moore | 128/784 |
| 4,570,642 | 2/1986 | Kane et al. | 128/785 |
| 4,602,645 | 7/1986 | Barringotn et al. | 607/122 |
| 4,603,705 | 8/1986 | Speicher et al. | 128/786 |
| 4,624,265 | 11/1986 | Grassi | 128/784 |
| 4,624,266 | 11/1986 | Kane | 128/785 |
| 4,627,439 | 12/1986 | Harris | 128/419 |
| 4,633,880 | 1/1987 | Osypka et al. | 128/642 |
| 4,646,755 | 3/1987 | Kane | 128/785 |
| 4,649,937 | 3/1987 | DeHaan et al. | 128/784 |
| 4,649,938 | 3/1987 | McArthur | 128/785 |
| 4,662,377 | 5/1987 | Heilman et al. | 128/419 |
| 4,662,382 | 5/1987 | Sluetz et al. | 128/785 |
| 4,664,113 | 5/1987 | Frisbie et al. | 128/344 |
| 4,667,686 | 5/1987 | Peers-Travarton | 128/785 |
| 4,679,572 | 7/1987 | Baker | 128/786 |
| 4,721,115 | 1/1988 | Owens | 128/713 |
| 4,727,877 | 3/1988 | Kallok | 128/419 |
| 4,741,342 | 5/1988 | Stotts | 128/419 |
| 4,773,401 | 9/1988 | Citak et al. | 128/419 PG |
| 4,782,836 | 11/1988 | Alt | 128/419 |
| 4,784,161 | 11/1988 | Skalsky et al. | 128/785 |
| 4,799,486 | 1/1989 | DuFault | 128/419 |
| 4,799,493 | 1/1989 | DuFault | 128/705 |
| 4,817,608 | 4/1989 | Shapland et al. | 128/419 |
| 4,817,634 | 4/1989 | Holleman et al. | 128/784 |
| 4,819,661 | 4/1989 | Heil, Jr. et al. | 128/786 |
| 4,819,662 | 4/1989 | Heil, Jr. et al. | 128/786 |
| 4,827,932 | 5/1989 | Ideker et al. | 128/419 D |
| 4,858,623 | 8/1989 | Bradshaw et al. | 128/785 |
| 4,860,750 | 8/1989 | Frey et al. | 128/419 |
| 4,860,769 | 8/1989 | Fogarty et al. | 128/786 |
| 4,865,037 | 9/1989 | Chin et al. | 128/419 D |
| 4,876,109 | 10/1989 | Mayer et al. | 427/2 |
| 4,886,074 | 12/1989 | Bisping | 128/785 |
| 4,905,691 | 3/1990 | Rydell | 606/47 |
| 4,913,164 | 4/1990 | Greene et al. | 128/785 |
| 4,919,135 | 4/1990 | Phillips, Jr. et al. | 128/419 |
| 4,924,881 | 5/1990 | Brewer | 128/785 |
| 4,938,231 | 7/1990 | Milijasevic et al. | 128/784 |
| 4,944,300 | 7/1990 | Saksena | 128/419 |
| 4,953,551 | 9/1990 | Mehra et al. | 128/419 |
| 4,967,766 | 11/1990 | Bradshaw | 128/785 |
| 4,969,463 | 11/1990 | Dahl et al. | 128/419 |
| 4,971,070 | 11/1990 | Holleman et al. | 128/784 |
| 4,998,975 | 3/1991 | Cohen et al. | 128/419 D |
| 5,000,177 | 3/1991 | Hoffmann et al. | 128/419 |
| 5,016,645 | 5/1991 | Williams et al. | 128/784 |
| 5,016,646 | 5/1991 | Gotthardt et al. | 128/784 |
| 5,016,808 | 5/1991 | Heil, Jr. et al. | 228/176 |
| 5,020,544 | 6/1991 | Dahl et al. | 128/784 |
| 5,027,813 | 7/1991 | Pederson et al. | 128/419 |
| 5,044,375 | 9/1991 | Bach, Jr. et al. | 128/786 |
| 5,050,601 | 9/1991 | Kupersmith et al. | 128/419 |
| 5,056,516 | 10/1991 | Spehr | 128/419 |
| 5,063,932 | 11/1991 | Dahl et al. | 128/639 |
| 5,074,313 | 12/1991 | Dahl et al. | 128/784 |
| 5,076,272 | 12/1991 | Ferek-Petric | 128/419 |
| 5,076,285 | 12/1991 | Hess et al. | 128/186 |
| 5,083,562 | 1/1992 | de Coriolis et al. | 128/419 |
| 5,086,773 | 2/1992 | Ware | 128/419 |
| 5,105,826 | 4/1992 | Smits et al. | 128/784 |
| 5,107,834 | 4/1992 | Ideker et al. | 128/419 |
| 5,111,811 | 5/1992 | Smits | 128/419 |
| 5,111,812 | 5/1992 | Swanson et al. | 128/419 D |
| 5,129,404 | 7/1992 | Spehr et al. | 128/785 |
| 5,133,353 | 7/1992 | Hauser | 128/419 |
| 5,133,365 | 7/1992 | Heil, Jr. et al. | 128/786 |
| 5,137,019 | 8/1992 | Pederson et al. | 128/419 |
| 5,139,033 | 8/1992 | Everett et al. | 128/785 |
| 5,144,960 | 9/1992 | Mehra et al. | 607/123 |
| 5,152,299 | 10/1992 | Soukup | 128/785 |
| 5,165,403 | 11/1992 | Mehra | 128/419 D |
| 5,174,303 | 12/1992 | Schroeppel | 128/786 |
| 5,203,348 | 4/1993 | Dahl et al. | 128/784 |
| 5,209,229 | 5/1993 | Gilli | 128/419 |
| 5,217,028 | 6/1993 | Dutcher et al. | 128/785 |
| 5,230,337 | 7/1993 | Dahl et al. | 607/5 |
| 5,235,976 | 8/1993 | Spinelli | 607/25 |
| 5,255,693 | 10/1993 | Dutcher et al. | 607/120 |
| 5,259,394 | 11/1993 | Bens | 607/127 |
| 5,259,395 | 11/1993 | Li | 607/131 |
| 5,261,395 | 11/1993 | Oleen et al. | 607/15 |
| 5,261,400 | 11/1993 | Bardy | 607/5 |
| 5,269,319 | 12/1993 | Schulte et al. | 128/786 |
| 5,271,417 | 12/1993 | Swanson et al. | 607/122 |
| 5,282,845 | 2/1994 | Bush et al. | 607/128 |
| 5,284,136 | 2/1994 | Hauck et al. | 607/24 |
| 5,300,106 | 4/1994 | Dah et al. | 607/119 |
| 5,300,108 | 4/1994 | Rebell et al. | 607/127 |
| 5,300,110 | 4/1994 | Latterell et al. | 607/130 |
| 5,314,459 | 5/1994 | Swanson et al. | 607/122 |
| 5,314,462 | 5/1994 | Heil et al. | 607/128 |
| 5,314,464 | 5/1994 | KenKnight et al. | 607/132 |
| 5,318,597 | 6/1994 | Hauck et al. | 607/20 |
| 5,324,327 | 6/1994 | Cohen | 607/122 |
| 5,330,512 | 7/1994 | Hauck et al. | 607/28 |
| 5,342,407 | 8/1994 | Dahl et al. | 607/129 |
| 5,342,414 | 8/1994 | Mehra | 607/127 |
| 5,344,439 | 9/1994 | Otten | 607/126 |
| 5,358,516 | 10/1994 | Myers et al. | 607/116 |
| 5,360,442 | 11/1994 | Dahl et al. | 607/129 |
| 5,366,496 | 11/1994 | Dahl et al. | 607/132 |
| 5,370,663 | 12/1994 | Lin | 607/5 |
| 5,374,286 | 12/1994 | Morris | 607/119 |
| 5,383,908 | 1/1995 | Sweeney et al. | 607/5 |
| 5,385,574 | 1/1995 | Hauser et al. | 607/4 |
| 5,391,190 | 2/1995 | Pederson et al. | 607/23 |
| 5,391,200 | 2/1995 | KenKnight et al. | 607/129 |
| 5,397,342 | 3/1995 | Heil, Jr. et al. | 607/129 |
| 5,405,373 | 4/1995 | Petersson et al. | 607/121 |
| 5,411,527 | 5/1995 | Alt | 607/5 |
| 5,411,544 | 5/1995 | Mar et al. | 607/122 |
| 5,413,593 | 5/1995 | Spinelli et al. | 607/27 |
| 5,425,755 | 6/1995 | Doan | 607/119 |
| 5,425,756 | 6/1995 | Heil, Jr. et al. | 607/128 |
| 5,431,693 | 7/1995 | Schroeppel | 607/28 |
| 5,433,730 | 7/1995 | Alt | 607/5 |
| 5,443,485 | 8/1995 | Housworth et al. | 607/28 |

| | | | |
|---|---|---|---|
| 5,447,533 | 9/1995 | Vachon et al. | 607/120 |
| 5,447,534 | 9/1995 | Jammet | 607/127 |
| 5,456,699 | 10/1995 | Armstrong | 606/108 |
| 5,456,706 | 10/1995 | Pless et al. | 607/122 |
| 5,456,708 | 10/1995 | Doan et al. | 607/127 |
| 5,476,501 | 12/1995 | Stewart et al. | 607/127 |
| 5,476,502 | 12/1995 | Rubin | 607/127 |
| 5,486,202 | 1/1996 | Bradshaw | 607/37 |
| 5,492,119 | 2/1996 | Abrams | 128/642 |
| 5,496,362 | 3/1996 | KenKnight et al. | 607/129 |
| 5,500,008 | 3/1996 | Fain | 607/5 |
| 5,514,174 | 5/1996 | Heil, Jr. et al. | 607/128 |
| 5,522,874 | 6/1996 | Gates | 607/127 |
| 5,527,344 | 6/1996 | Arzbaecher et al. | 607/3 |
| 5,529,579 | 6/1996 | Alt et al. | 607/36 |
| 5,531,780 | 7/1996 | Vachon | 607/120 |
| 5,534,022 | 7/1996 | Hoffmann et al. | 607/122 |
| 5,540,723 | 7/1996 | Ideker et al. | 607/7 |
| 5,545,188 | 8/1996 | Bradshaw et al. | 607/37 |
| 5,545,202 | 8/1996 | Dahl et al. | 607/129 |
| 5,545,205 | 8/1996 | Schulte et al. | 607/123 |
| 5,554,178 | 9/1996 | Dahl et al. | 607/122 |
| 5,571,162 | 11/1996 | Lin | 607/122 |
| 5,578,062 | 11/1996 | Alt et al. | 607/5 |
| 5,578,068 | 11/1996 | Laske et al. | 607/126 |
| 5,603,732 | 2/1997 | Dahl et al. | 607/122 |
| 5,607,455 | 3/1997 | Armstrong | 607/8 |
| 5,620,451 | 4/1997 | Rosborough | 606/108 |
| 5,628,778 | 5/1997 | Kruse et al. | 607/123 |
| 5,628,779 | 5/1997 | Bornzin et al. | 607/123 |
| 5,643,328 | 7/1997 | Cooke et al. | 607/36 |
| 5,654,030 | 8/1997 | Munshi et al. | 427/2.24 |
| 5,674,274 | 10/1997 | Morgan et al. | 607/123 |
| 5,683,443 | 11/1997 | Munshi et al. | 607/121 |
| 5,683,447 | 11/1997 | Bush et al. | 607/126 |
| 5,700,283 | 12/1997 | Salo | 607/17 |
| 5,713,926 | 2/1998 | Hauser et al. | 607/5 |
| 5,718,720 | 2/1998 | Prutchi et al. | 607/28 |
| 5,720,768 | 2/1998 | Verboven-Nelissen | 607/9 |
| 5,730,125 | 3/1998 | Prutchi et al. | 128/637 |
| 5,749,911 | 5/1998 | Westlund | 607/36 |
| 5,769,881 | 6/1998 | Schroeppel et al. | 607/123 |
| 5,772,693 | 6/1998 | Brownlee | 607/123 |
| 5,776,072 | 7/1998 | Hsu et al. | 600/518 |
| 5,782,884 | 7/1998 | Stotts et al. | 607/17 |
| 5,782,898 | 7/1998 | Dahl et al. | 607/119 |
| 5,792,183 | 8/1998 | Esler | 607/4 |
| 5,792,205 | 8/1998 | Alt et al. | 607/32 |
| 5,797,967 | 8/1998 | KenKnight | 607/4 |
| 5,800,495 | 9/1998 | Machek et al. | 607/116 |
| 5,814,088 | 9/1998 | Paul et al. | 607/28 |
| 5,817,130 | 10/1998 | Cox et al. | 607/5 |
| 5,843,153 | 12/1998 | Johnston et al. | 607/122 |
| 5,851,227 | 12/1998 | Spehr | 607/126 |
| 5,871,529 | 2/1999 | Bartig et al. | 607/122 |
| 5,871,532 | 2/1999 | Schroeppel | 607/128 |
| 5,876,431 | 3/1999 | Spehr et al. | 607/126 |
| 5,885,221 | 3/1999 | Hsu et al. | 600/515 |
| 5,916,238 | 6/1999 | Hauser et al. | 607/5 |
| 5,916,243 | 6/1999 | KenKnight et al. | 607/129 |

OTHER PUBLICATIONS

Jones, D.L., et al., "Internal Cardiac Defibrillation in Man: Pronounced Improvement with Sequential Pulse Delivery to Two Different Lead Orientations", *Circulation*, vol. 73, No. 3, p. 484–491 (Mar. 1986).

U.S. Patent Application Serial No. 09/121,020 filed on Jul. 22, 1998 entitled "Single Pass Defibrillation/Pacing Lead with Passively Attached Electrode for Pacing and Sensing".

U.S. Patent Application Serial No. 09/121,018 filed on Jul. 22, 1998 entitled "Single Pass Defibrillation/Pacing Lead with Passively Attached Electrode for Pacing and Sensing".

U.S. Patent Application Serial No. 09/121,019 filed on Jul. 22, 1998 entitled "Single-Pass Endocardial Lead for Multi-Site Atrial Pacing".

U.S. Patent Application Serial No. 09/121,288 filed on Jul. 22, 1998 entitled "High Impedance Electrode Tip".

U.S. Patent Application Serial No. 09/120,824 filed on Jul. 22, 1998 entitled "Single Pass Lead System".

U.S. Patent Application Serial No. 09/121,005 filed on Jul. 22, 1998 entitled "Single Pass Lead and System with Active and Passive Fixation Elements".

SINGLE PASS LEAD HAVING RETRACTABLE, ACTIVELY ATTACHED ELECTRODE FOR PACING AND SENSING

RELATED APPLICATIONS

This patent application is related to applications entitled "SINGLE PASS DEFIBRILLATION/PACING LEAD WITH PASSIVELY ATTACHED ELECTRODE FOR PACING AND SENSING" having Ser. Nos. 09/121,018 and 09/121,020, which are assigned to a common assignee and is filed on a date even herewith. The related application is incorporated herein by reference.

FIELD OF THE INVENTION

The present invention relates to the field of leads for correcting arrhythmias of the heart. More particularly, this invention relates to a lead having an electrode for more effective delivery of electrical charges to the heart.

BACKGROUND OF THE INVENTION

Electrodes implanted in the body for electrical cardioversion or pacing of the heart are well known. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm. Electrodes have also been used to sense and deliver pacing pulses to the atrium and ventricle. The electrode in the atrium senses the electrical signals that trigger the heartbeat. The electrode detects abnormally slow (bradycardia) or abnormally fast (tachycardia) heartbeats. In response to the sensed bradycardia or tachycardia condition, a pulse generator produces pulses or signals to correct the condition. The same node used to sense the condition is also used in the process of delivering a corrective pulse or signal from the pulse generator of the pacemaker.

There are four main types of pulses which are delivered by a pulse generator. Two of the signals or pulses are for pacing the heart. First of all, there is a pulse for pacing the heart when it is beating too slowly. The pulses trigger the heart beat. The pulses are delivered at a rate to increase the heart rate to a desired level. The second type of pacing, called antitachycardia pacing, is used on a heart that is beating too fast. In antitachycardia pacing, the pacing pulses are delivered initially at a rate faster than the beating heart. The rate of the pulses is then slowed until the heart rate is at a desired level. The third and fourth type of pulses are used when the heart is beating too fast and the heart is fibrillating. The third type is called cardioversion. This is delivery of a relatively low energy shock, typically in the range of 0.75 to 1 joule, to the heart. The fourth type of pulse or signal is a defibrillation signal which is the delivery of a high energy shock, typically up to 34 joules, to the heart.

Sick sinus syndrome and symptomatic AV block constitute the major reasons for insertion of cardiac pacemakers today. Cardiac pacing may be performed by the transvenous method or by electrodes implanted directly onto the epicardium. Transvenous pacing may be temporary or permanent. In temporary transvenous pacing, an electrode lead is introduced into a peripheral vein and fluoroscopically positioned against the endocardium. The external terminals of the leads are connected to an external cardiac pacemaker which has an adjustable rate and milliamperage control. Temporary transvenous pacing is utilized (1) prior to the insertion of a permanent pacing system and (2) in situations in which the indication for pacing is judged to be reversible (drug-induced AV block or bradycardia) or possibly irreversible and progressive (AV and bundle branch blocks associated with myocardial infarction).

Permanent transvenous pacing is implanted under sterile surgical conditions. An electrode lead is generally positioned in the right ventricle and/or in the right atrium through a subclavian vein, and the proximal electrode terminals are attached to a pacemaker which is implanted subcutaneously.

Some patients require a pacing system to correct an abnormally slow heart (bradycardia condition) as well as a defibrillation system to detect when the heart starts beating abnormally fast (tachycardia condition) and to defibrillate or deliver a pulse to the heart to correct the abnormally fast heartbeat. In the past, a common practice for a patient having both of these conditions would be to provide two different leads attached to the heart. One would be implanted for delivering pacing signals to the heart to correct for the bradycardia condition. A separate lead would be implanted to sense a fast beating heart and defibrillate the heart to correct for the tachycardia condition. One lead is placed in the atrium and the other lead is placed in the ventricle.

Having two separate leads implanted within the heart is undesirable for many reasons. Among the many reasons are that the implantation procedure for implanting two leads is more complex and also takes a longer time when compared to the complexity and time needed to implant a single lead. In addition, two leads may interact with one another after implantation or in vivo which can result in dislodgment of one or both of the leads. In vivo interaction may also cause abrasion of the insulative layer along the lead which can result in an electrical failure of one or both of the leads. Another problem is that as more leads are implanted in the heart, the ability to add leads is restricted. Two separate leads also increase the risk of infection and may result in additional health care costs associated with implantation and follow-up.

Because of these problems, a single lead having electrodes for both pacing and sensing in both chambers of the heart has been used. These leads are called single pass lead designs. Current single pass lead designs have problems. One of the more significant problems is that current single pass lead designs utilize "floating" electrodes or electrodes which are not attached to the endocardial wall of the heart. The floating electrodes lay in the blood pool or against the endocardial wall of the heart and the electrode may move slightly within the heart. The electrode positioned within the atrium of a single-pass endocardial lead generally is an electrically conductive cylindrical ring or semicylindrical ring structure, which does not allow for tissue ingrowth into the electrode. Since the location of the electrodes is not fixed with respect to the atrial wall, the electrical performance of these electrodes varies and is generally less than optimal. Both the electrical sensing capability as well as the pacing delivery capability of such electrodes are suboptimal. The pacing parameters of such a floating electrode are also suboptimal.

Some atrial leads have passive fixation elements that affix to the atrium over time. A problem with these leads is that the electrodes are much more likely to be displaced from the wall of the atrium than those that have an active fixation element. When the electrodes are placed far from the wall, there can be some fairly substantial effects. For example might be unable to sense a tachycardia condition. Another example might be that signals for pacing may be ineffective. Additional power may have to be used to pace the heart thereby depleting energy from the battery of the pulse generator of the pacing system.

There is a real need for a single-pass endocardial pacing lead that has an electrode for active fixation to the wall of the atrium of the heart. A single-pass lead equipped with such an electrode would allow for better sensing capability and better pacing delivery to the heart. In addition, there is a need for a single-pass lead having an electrode for positioning within the atrium that allows for tissue ingrowth. Tissue ingrowth further enhances the electrical performance of the electrode. In addition, the lead and electrode is further stabilized within the heart as a result of tissue ingrowth. There is also a need for a single-pass endocardial lead which has an electrode for placing within the right atrium of the heart that accommodates eluting anti-inflammatory drugs.

SUMMARY OF THE INVENTION

A single-pass endocardial lead electrode adapted for implantation in the heart and for connection to a system for monitoring or stimulating cardiac activity includes a lead body with a circumferential outer surface. The lead includes a first distal end electrode or pair of electrodes for positioning in the ventricle and a second proximal electrode or pair of electrodes for positioning in the atrium. The second electrode or pair of electrodes are adapted for positioning and fixation to the wall of the atrium of the heart. An active fixation element is used as part of the second electrode or electrode pair. The lead body also may include a curved portion which facilitates the positioning and fixing of the second electrode or second pair of electrodes. The lead body also includes at least one recess for positioning an active fixation element within the recess.

In another embodiment, the recess is able to house the active fixation electrode as well as a portion of a lead body associated with the atrium (atrial lead body). By moving the terminal pin with respect to a yoke, the lead body is moved out of the recess. The atrial lead body can be a straight lead or a J-shaped lead. The type of atrial lead body used will depend on the placement of the lead within the atrium of the heart and the preference of the surgeon doing the placement. The advantage is that the active fixation electrode is placed into the recess during placement of the lead to prevent it from attaching inadvertently to the subclavian vein or other tissue while it is being inserted.

One of the embodiments includes the use of an active fixation electrode that can be controllably moved from a recessed position to an attachment position by rotating the terminal pin attached to the conductor coil which is attached to the body of the active fixation electrode.

Advantageously, the electrodes are attached to the endocardium so that the electrical signals received from the heart are better than with floating, unattached electrodes. In addition, the active fixation electrodes can be placed into a recess so that mechanisms, such as a helical hook, used to attach the electrode to the wall of the heart will not catch undesired tissue. A further advantage is that only one lead needs to be placed into the patient to do both sensing and pacing of all types. The lead can also be shaped to facilitate placement of the lead.

The extendable portion of the lead is mechanically isolated from the main lead body so that the helical screw or hook can turn independently of the lead body. In other words, the body of the lead does not need to be turned to affix the helical screw to the heart.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Curved Lead with Atrial Active Fixation Element

This invention is directed toward an active fixation element used in several types of leads. One type of lead will be described first to not only describe one embodiment of the invention but to also set forth generally the environment of the invention. After describing the first lead embodiment, the active fixation element will be detailed. Next, the other embodiments of the lead will be described.

Figure 1:
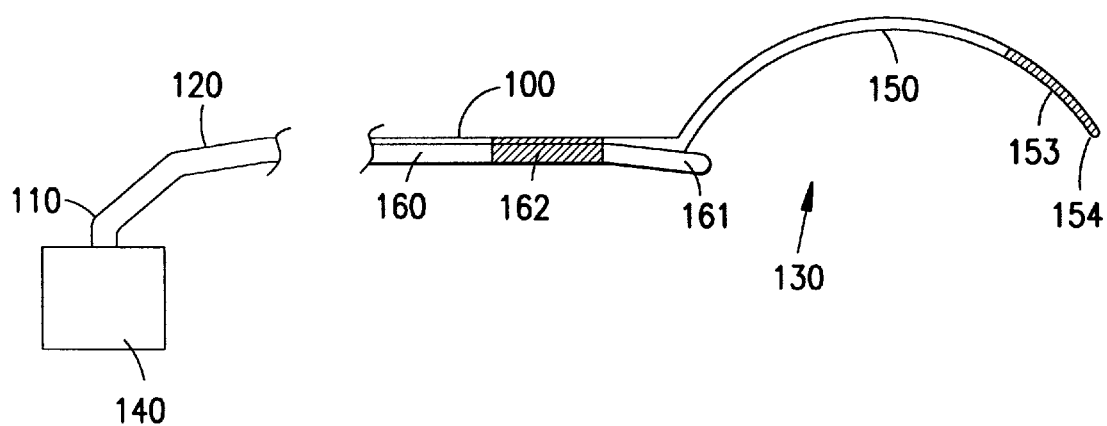
FIG. 1 is a side view of the single-pass endocardial lead for electrically stimulating the heart.

FIG. 1 is a side view of one type of lead 100 for delivering electrical pulses to stimulate the heart. The lead 100 is comprised of a connector terminal 110 and a lead body 120. The lead 100 attaches to a pulse sensor and generator 140. The lead body has a number of electrodes in the distal end 130 which is implanted within the heart. The connector terminal 110 electrically connects the various electrodes and conductors within the lead body to a pulse sensor and generator 140. The pulse sensor and generator 140 contains electronics to sense various pulses of the heart and also produce pulsing signals for delivery to the heart. The pulse sensor and generator 140 also contains electronics and software necessary to detect certain types of arrhythmias and to correct for them. Physicians are able to program the pulse sensor and generator to correct a particular arrhythmia that the patient may have. It should be noted that there are numerous types of connector terminals which connect to a pulse sensing and generating unit 140. The lead terminal connector 110 provides for the electrical connection between the electrodes on the lead 100 and pulse generator 140. The connector terminal end 10 shown is designed to international IS-1 Standard ISO 5841-3(E).

The lead body 120 is cylindrical in shape. The lead body 120 is a tubing material formed from a polymer biocompatible for implantation, and preferably the tubing is made from a silicone rubber polymer. The silicone rubber polymer tubing contains several electrical conductors. The electrical conductors are made of a highly conductive, highly corrosion-resistant material which is formed into a helix. Several separate electrical conductors are housed within the lead body 120. When there is more than one such electrical conductor within the lead body 120, the lead is called a multifilar lead. The electrical conductors carry current and signals between the pulse sensor and generator 140 and the electrodes located at the distal end 130 of the lead 100.

After the lead 100 has been implanted, the distal end 130 of the lead body 120 is situated within the heart. The distal end 130 of the lead body 120 includes a curved or bias portion 150 and a straight portion 160.

After implantation, the curved or biased portion 150 will generally be located in the right ventricle of the heart. The straight portion 160 of this lead body will generally be located in the right atrium. The distal end 130 of the lead 100 has four electrodes. The first electrode 154 is provided at the farthest distal end of the lead for the purpose of delivering ventricular pacing therapy. The first electrode 154 is generally called the distal electrode. A second electrode 153 is located near the first or distal electrode 154 and can be used as a counter electrode for electrode 154 or as a current source for defibrillation therapy. This electrode 153 is sometimes referred to as a ventricular shocking coil. A third electrode 161 is located at a more proximal position for the purpose of delivering atrial pacing therapy. This electrode 161 is intended to be actively attached to the atrial wall of the heart. The third electrode 161 is also referred to as the proximal electrode. A fourth electrode 162 is located near the electrode 161 and can be used as a counter electrode for electrode 161 or as part of a defibrillation therapy system. The fourth electrode 162 is sometimes called the SVC shocking coil. The lead 100 may be generally described as a tachycardia or tachy lead. The shocking coils 153 and 162 are electrically conductive rings made of an alloy of platinum and iridium which is highly conductive and highly resistant to corrosion. The electrode 161 uses the active fixation element described below. The electrode 154 may include an active fixation or passive fixation portion. It should be noted that the lead shown and described above is a bipolar lead in that the positive and negative portions of a circuit are located in the lead body 100. It should be noted that this lead may also be made a unipolar lead. In other words, one electrode of the lead body 100 can be the shocking coil and the other electrode can be the signal generator.

The shape of the curved portion 150 of the lead is important. The relaxed shape of the lead body 120 conforms to the shape the lead is expected to take after implantation. The distal portion of the straight portion 160 and the proximal portion of the curved portion 150 are biased to conform to the mid-portion of the atrial wall. This shape facilitates the placement of electrode 161 against the atrial wall during implantation. Furthermore, because the natural unstressed shape of the lead before implantation is approximately the same after implantation, this reduces the nominal residual stresses in the lead body. Also, this will reduce the nominal forces between the atrial wall and the point of attachment of the electrode 161 in the atrium. The shape of the middle and end portions of portion 150 conforms to the shape of the upper ventricular chamber below the tricuspid valve and ventricular septal wall. This shape will tend to cause the lead 100 to lie across the top of the ventricle in a gradual arc with the electrode 153 lying against the ventricular septum and electrode 154 resting in the ventricular apex. This lead position is advantageous because the arc shape will tend to reduce the transmitted forces between the lead fixation points at electrode 161 in the atrium and electrode 154 in the ventricle as they move relative to each other during heart rhythm. This preformed shape will ease the surgeon's task of positioning of lead 100 and, particularly, of the electrode end 130 such that less time is required and the placement procedure is less prone to error.

Figure 2:
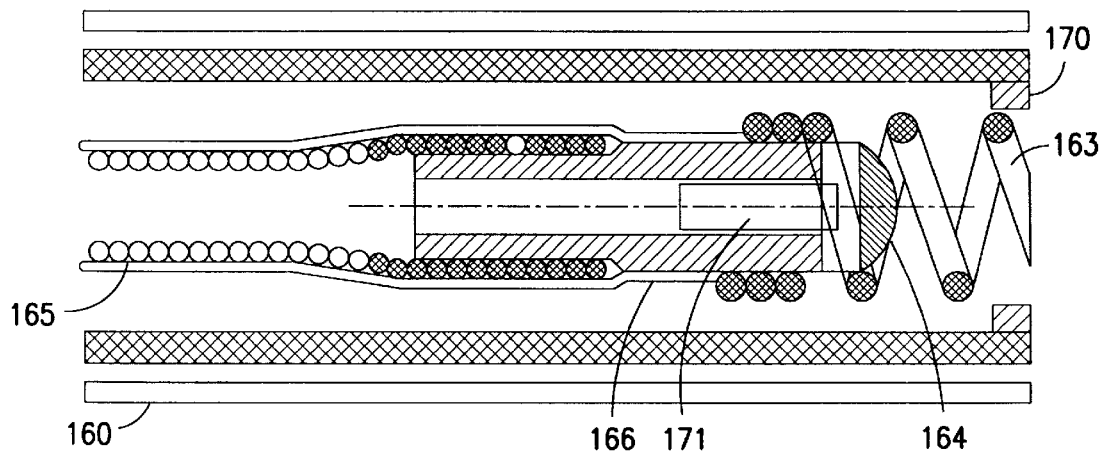
FIG. 2 is a cross section view of the atrial electrode of the single-pass endocardial lead showing the active attachment element in a retracted position.
Figure 3:
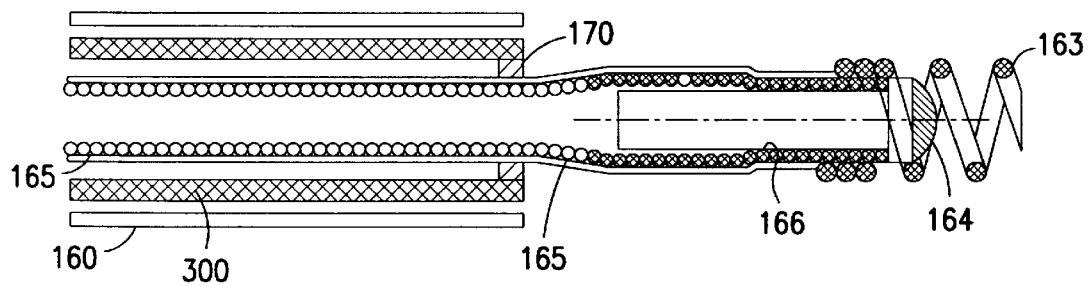
FIG. 3 is a cross section view of the atrial electrode portion of the lead showing the active attachment element for active attachment to the atrial wall of the heart in an extended position.

As mentioned previously, electrode 161 is designed to be attached to the wall of the atrium of the heart. FIG. 2 shows electrode 161 in a recessed position. FIG. 3 shows electrode 161 actively attached to the wall of the atrium. In this embodiment, the electrode 161 includes an active fixation screw 163 which is a helical screw. The atrial electrode 161 is configured to initially rest inside the lead body 120, and then extend and rotate independent of the lead body 120 for atrial attachment. FIG. 2 shows the electrode 161 and the fixation screw 163 resting within the lead body. A seal 170 is shown in FIGS. 2 and 3. The seal 170 prevents body fluids from traveling into the recess in the lead body. The seal 170 is made of a biocompatible material such as silicone rubber. The seal 170 may take any appropriate shape. In this instance, the seal 170 is shaped as a permanent O-ring affixed to the recess in the lead body. This covered position of the electrode 161 and active fixation screw 163 makes the lead placement process easier since the atrial electrode 161 does not snag the vein during initial venous access and subsequent movement of the lead to the heart. The seal 170 can also be used to hold a lubricant 300 within the recess of the body of the lead. The lubricant 300 will allow the atrial electrode 161 to move from inside the recess to outside the recess with greater ease. The lubricant can be a substance such as fluorosilicone which is biocompatible.

Figure 4:
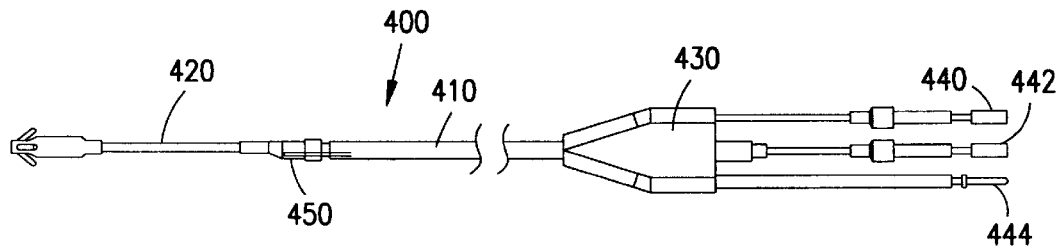
FIG. 4 is a side view of another embodiment of a lead for active fixation attachment to the atrial wall of the heart.
Figure 5:
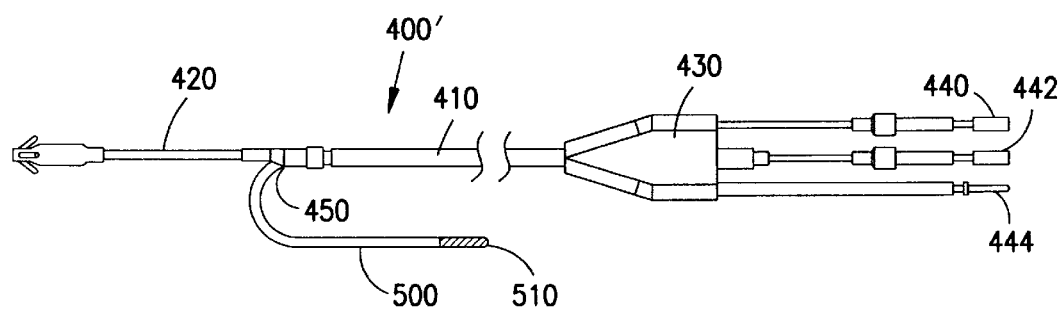
FIG. 5 is a side view of the embodiment of the lead shown in FIG. 4 with the atrial lead body in an extended position for active attachment to the atrial wall of the heart.

FIG. 3 shows the electrode 161 extended from the lead body. The electrode 161 and active fixation screw 163 move independent of the lead body. This relative movement allows the electrode to come in contact with the atrial wall without manipulation of the lead body 120. The electrode 161 can then be fixed by rotating the atrial electrode 161 and attached fixation screw 163. The fixation screw 163 of the atrial electrode 161 can be advanced and retracted independent of rotation of the lead body. The active fixation screw and attached electrode are controlled from the terminal end. This is shown by turning briefly to FIGS. 4 and 5. In FIGS. 4 and 5, there is a lead housed within a recess 450 in the lead body 410. The lead housed within the recess 450 can be moved in and out of the recess 450 by moving a terminal end 442 longitudinally with respect to the lead body 410. As shown in FIG. 4, the lead is within a recess when the terminal end 442 is positioned even with the other terminal ends. When the terminal end is moved toward the distal end of the lead, the lead within the recess 450 is moved out of the recess 450. As shown in FIG. 3, this additional degree of freedom allows for movement of the lead body relative to the fixed atrial electrode 161 without unscrewing (or over-screwing) the electrode from the endocardial tissue.

Returning to FIG. 3, as mentioned previously, the electrically conductive portion 164 which either senses electrical energy produced by the heart or delivers pacing signals to the heart is a small radius electrode. The electrode 161 has a diameter in the range of 0.024 inches to 0.050 inches. The advantage of this small radius is ease of venous access and small surface area resulting in high impedance for saving energy. Saving energy makes the battery used to power the pulse generator 140 last longer.

Also shown in FIGS. 2 and 3 is a multifilar coil 165 and an electrically conductive sleeve 166. The conductive sleeve 166 has the smaller radius electrode tip 164 attached at one end of the sleeve. At the other end of the sleeve 166, the multifilar coil 165 is attached. The multifilar coil includes at least one conductor which is used to carry electrical signals to and from the electrode tip 164.

It is contemplated that slight variations in the design could be used for a particular application as required. One such variation would be the provision of steroid elution from any of the electrodes 153, 154, 161 and 162. Steroid elution can be provided by using one or more of the steroid-releasing technologies such as sleeves or collars positioned in close proximity to the electrodes or by the use of internalized steroid-containing plugs (171). Steroids are generally used in order to reduce the inflammation associated with attaching an electrode to the endocardial wall of the heart. By reducing the inflammation at the time of implantation, the threshold values associated with the electrodes are usually lower when compared to threshold values associated with electrodes that did not elute a steroid over the attachment site. An example of the composition of at least one collar is dexamethasone acetate in a simple silicone medical adhesive rubber binder or a steroid-releasing plug similarly fabricated.

Of course, for the active fixation embodiment of this invention shown in FIGS. 1–3, various advancing and locking mechanisms can be used to manipulate the atrial electrode 161 from the proximal end of the lead during implantation.

Various shapes of stylets can be placed within the lead to advance and position the lead within the endocardial wall of the heart. Once positioned correctly, an active fixation element is used to secure the electrode to the wall of the heart. A locking mechanism can be employed to keep the fixation element from moving from its attached position on the heart.

Quad Lumen with Yoke and Active Fixation

Figure 6:
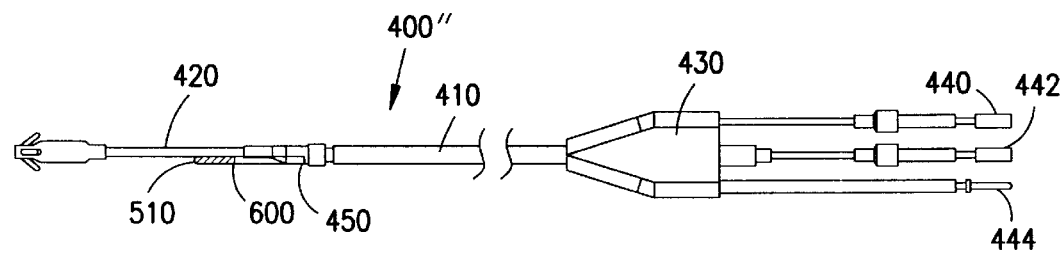
FIG. 6 is a side view of the embodiment of the lead shown in FIG. 4 with the atrial lead body in an extended position for active attachment to the atrial wall of the heart.

FIGS. 4, 5, and 6 show several other closely related preferred embodiments of the invention. FIG. 4 is a side view of a lead 400 which includes an active fixation element for attachment to the atrial wall of the heart. The lead 400 includes a main lead body 410, an atrial lead body (also shown in FIGS. 5 and 6) and a ventricle lead body 420. The main lead body 410 is attached to a yoke 430. The yoke 430 acts as a strain reliever and also has a series of terminal pins 440, 442 and 444 attached to the yoke/strain reliever 430. The terminal pins 440, 442 and 444 are attached to the pulse generator (not shown). The main lead body 410 is longer than as shown; a break has been put into the main lead body 410 to illustrate that the main lead body 410 is longer than that shown in FIG. 4. The main lead body 410 includes a recess 450. The atrial lead body (shown in FIGS. 5 and 6) fits within the recess 450 in the main lead body 410. When the atrial lead body is housed within the recess 450, an active fixation element on the end of the atrial lead body and associated with the proximate electrode is also housed within the recess. Advantageously, the active fixation element will not hook or snag tissue when it is housed within the recess 450. Typically, the atrial lead body is pulled back or housed within the recess 450 when the lead 400 is being surgically implanted into the patient. Typically, the lead 400 is placed in the subclavian vein of the patient and then passed through the subclavian vein to the inner chambers of the heart. Once the lead and, more specifically, the distal electrode and the proximal electrode are within the ventricle and atrium of the heart, the various leads are removed from their respective recesses so that a surgeon can attach them to the inner wall of the heart.

FIG. 5 is a side view of the embodiment of a lead 400 shown in FIG. 4. FIG. 5 has a J-shaped atrial lead body 500 which emerges from the recess 450 in the main body of the lead 410. On the end of the atrial lead 500 is an active fixation element 510. The active fixation element 510 typically includes a helically shaped hook for screwing into the atrium of the heart. The J-shape of the lead facilitates positioning of the end of the electrode having the active fixation element 510 to a desired position within the atrium. The J-shape eases positioning within the atrium of the heart when certain portions of the atrium are the target for connection of the active fixation element 510. Once properly positioned, a surgeon can turn the active fixation element 510 causing it to hook the tissue in the inner wall of the heart. The atrial lead 500 is moved with respect to the recess by pushing the terminal pin from 442 forward with respect to the yoke 430. A conductor connects the terminal pin 442 and the active fixation element 510. By moving the terminal pin 442 inward with respect to the yoke 430, the conductor moves with respect to the main body 410 of the lead 400'. This causes the atrial lead body 500 to emerge or pass through or pass out of the recess 450 in the main body 410. The terminal pin 442 and the active fixation element attached to it move independently of the lead body 400. Twisting the terminal pin causes the active fixation element 510 on the atrial lead 500 to turn and affix itself to the atrial wall of the heart. A locking mechanism may be provided to prevent the active fixation element 510 from "backing out" after it has been affixed to the wall. The atrial lead 500 is prestressed so that it will take the J-shape upon leaving or coming out of the recess 450.

FIG. 6 is a side view of another embodiment of the lead shown in FIG. 4. In this particular embodiment, the lead 400" has a straight atrial lead 600 which comes out of the recess 450 in the main lead body 410. The position of the atrial lead 600 is controlled by movement of the terminal pin 442 with respect to the yoke 430. Moving the terminal pin with respect to the yoke 430 causes the atrial lead 600 to come out of the recess 450. An active fixation element 510 is positioned on the end of the atrial lead 600. Once the surgeon positions the atrial lead 600 and the active fixation element 510 at the end of the atrial lead in a proper position or desired position, the active fixation element 510 is used to attach the proximal electrode to the endocardial wall of the atrium.

Figure 7:
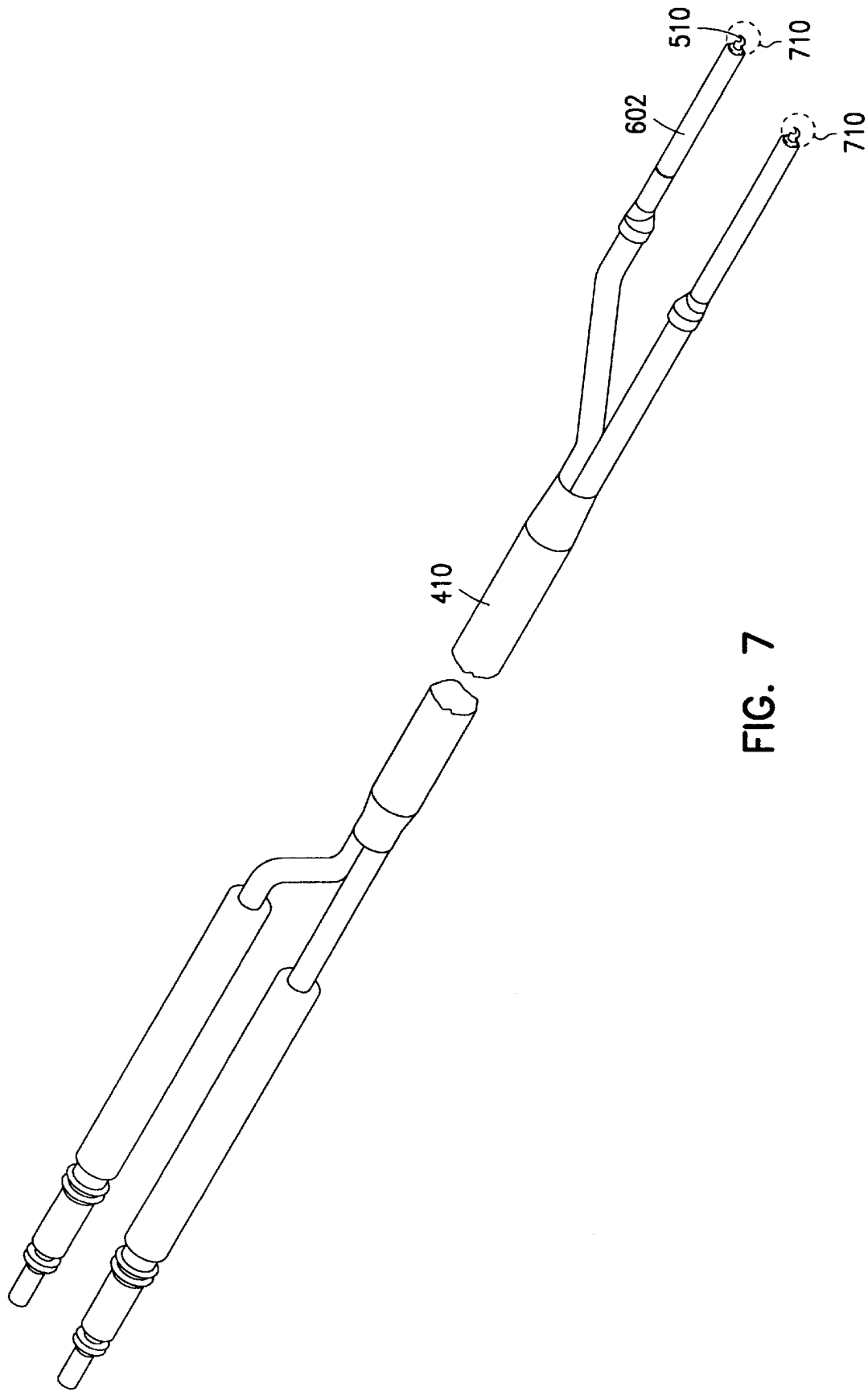
FIG. 7 is a perspective view of another embodiment of a lead for active fixation to the wall of the heart.

FIG. 7 shows another embodiment of the invention wherein the atrial lead portion 600 does not have the ability to move in and out of a recess. Rather, the atrial lead 600 is permanently extended with respect to the lead body 410. The active fixation element 510 on the atrial lead 600 is covered with a dissolvable coating 710, such as mannitol. The dissolvable coating 710 remains intact during insertion of the lead 400" through the subclavian vein and into the heart. The dissolvable coating 710 prevents the active fixation element 510 from catching tissue in the vein during insertion. The coating dissolves to expose active fixation element 510 and allow it to be turned into the atrial wall of the heart. In FIG. 7, the dissolvable coating 710 is depicted by a dotted line enclosure around the active fixation element 510. Both leads have an exposed active fixation element and both are actually covered with the dissolvable coating. The terminal pin 442 is turned to rotate the active fixation element 510. The active fixation element 510 can be turned or rotated independently of the lead body 410.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A single pass dual chamber lead system comprising:
   a signal generator for producing pulses to apply to the heart;
   a main lead body adapted to carry signals to and from the heart, the main lead body extending from a proximal end to a distal end;
   a first electrode having a first lead body and an active fixation portion, said main lead body having a first recess therein housing the first electrode, the first electrode and the first lead body capable of moving between a first recessed position within said first recess and a second extended position outside the first recess so that the active fixation portion of the first electrode is adapted to attach to a wall of the heart;
   a second electrode associated with the main lead body, the first electrode adapted to be housed with a first chamber of the heart and the second electrode adapted to be housed within a second chamber in the heart, said main lead body having a second recess therein housing the second electrode, the second electrode capable of moving between a first recessed position within said second recess and a second extended position outside the second recess so that the second electrode is adapted to attach to the wall of the heart; and
   wherein the main lead body has a single continuous curve disposed between the first electrode and the second electrode.

2. The system of claim 1 wherein one of the first electrode or the second electrode is a unipolar electrode.

3. The system of claim 1 wherein one of the first electrode or the second electrode is a bipolar electrode, said lead further comprising a third electrode paired and positioned near said bipolar electrode.

4. The system of claim 1 wherein the first electrode and the second electrode are bipolar electrodes, said lead further comprising:
   a third electrode paired with one of the first or second electrodes; and
   a fourth electrode paired with the other of the first or second electrodes.

5. The system of claim 1 wherein the position of one of the first or second electrodes can be controlled from the proximal end of the main lead body.

6. The system of claim 5 wherein the second electrode further includes an active fixation element, said active fixation element controllable from the terminal end of the main lead body.

7. The system of claim 6 wherein the first electrode is positionable in a first position within the recess when the lead is being surgically inserted.

8. The system of claim 7 wherein the first electrode is positionable in a second position outside of the recess, the position of the electrode controllable from the proximal end of the main lead body.

9. The system of claim 7 wherein the main lead body includes a seal near the opening of the recess to prevent the flow of body fluids into the lead.

10. The system of claim 7 wherein the main lead body includes a lubricant within the recess.

11. The system of claim 6 wherein the main lead body is shaped to bias the first electrode with the active fixation portion toward an atrial wall of the heart.

12. The system of claim 1 wherein the lead body of the other of first or second electrodes further comprises a plug of drug eluting material positioned within the lead body.

13. The system as recited in claim 12, wherein the main lead body has a single continuous curve disposed between the first electrode and the second electrode.

14. A lead comprising:
   a lead body extending from a proximal end to a distal end;
   a first electrode attached to the distal end of the lead body; and
   a second electrode attached to the lead body a selected distance away from the first electrode defining a portion of the lead body between the first electrode and the second electrode, wherein the entire portion of said lead body between the first electrode and the second electrode has a single continuous curve therein to facilitate positioning of the first electrode and the second electrode within two different chambers of a heart.

15. The lead of claim 14 further comprising a first fixation element for one of the first electrode or the second electrode.

16. The lead as recited in claim 14, wherein the first electrode and the second electrode are each placed adjacent to the single continuous curve.

17. The lead as recited in claim 14, wherein the lead body has a recess therein, the recess adapted for receiving the second electrode therein.

18. A system for detecting arrhythmias of the heart and for delivering signals to the heart, said system comprising:
   an electronics system further comprising,
      a cardiac activity sensor; and
      a signal generator which produces signals to stimulate the heart; and
   a lead adapted for implantation on or about the heart and for connection to the electronics system, said lead further comprising:
      a main lead body having a first recess therein;
      a supplemental lead body carrying a first electrode, said supplemental lead body capable of being moved between a first position substantially within the first recess, and a second position substantially outside the first recess;
      a second electrode attached to the main lead body; and
      wherein the main lead body has a single continuous curve disposed between the first electrode and the second electrode.

19. The system for detecting arrhythmias of the heart and for delivering signals to the heart of claim 18 further comprising a first fixation element positioned near the first electrode.

20. The system for detecting arrhythmias of the heart and for delivering signals to the heart of claim 18 further comprising a terminal end, said terminal end of the main lead body connecting the lead body with the signal generator, wherein the movement of the supplemental lead body can be controlled from the terminal end.

21. A method for inserting a dual chamber single pass lead into the heart comprising the steps of:
   inserting a stylet into the lead;
   placing a first electrode, a first electrode lead body, and an active fixation element into a retracted position within a first recess in a lead body of the single pass lead, wherein the entire first electrode is disposed within the first recess in the retracted position, the lead including a second electrode attached to the lead body a selected distance away from the first electrode defining a portion of the lead body between the first electrode and the second electrode, wherein the entire portion of said lead body between the first electrode and the second electrode has a single continuous curve;

inserting the lead into a vein and placing the lead within the heart, including positioning the first electrode and the second electrode within two different chambers of the heart;

moving the first electrode and active fixation element outward from the first recess; and attaching the active fixation element to an endocardial wall of the heart.

22. The method for inserting a dual chamber single pass lead of claim 21 further comprising:

controlling the movement of the active fixation element from a terminal end of the lead.

23. The method for inserting a dual chamber single pass lead of claim 22 wherein the controlling further comprises:

rotating a terminal pin associated with the first electrode to move the electrode from a recessed position to a tissue contact position.

24. The method for inserting a dual chamber single pass lead of claim 22 wherein controlling further comprises:

moving the terminal pin associated with the first electrode longitudinally to move the first electrode from a recessed position to a tissue contact position.

25. A single pass dual chamber lead system comprising:

a signal generator for producing pulses to apply to the heart;

a main lead body adapted to carry signals to and from the heart, the main lead body extending from a proximal end to a distal end;

a first electrode having a first lead body and an active fixation portion, said main lead body having a first recess therein housing the first electrode, the first electrode and the first lead body capable of moving between a first recessed position within said first recess and a second extended positioned outside the first recess so that the active fixation portion of the first electrode is adapted to attach to a wall of the heart, wherein the first electrode is positionable in the first recessed position when the lead is being surgically inserted;

a second electrode associated with the main lead body, the first electrode adapted to be housed with a first chamber of the heart and the second electrode adapted to be housed within a second chamber in the heart, said main lead body having a second recess therein housing the second electrode, the second electrode capable of moving between a first recessed position within said second recess and a second extended position outside the second recess so that the second electrode is adapted to attach to the wall of the heart; and wherein the main lead body includes a seal near the opening of the recess to prevent the flow of body fluids into the lead.

26. The system of claim 25, wherein the first electrode is positionable in a first position within the recess when the lead is being surgically inserted.

27. The system of claim 25, wherein the first electrode is positionable in a second position outside of the recess, the position of the electrode controllable from the proximal end of the main lead body.

28. A single pass dual chamber lead system comprising:

a signal generator for producing pulses to apply to the heart;

a main lead body adapted to carry signals to and from the heart, the main lead body extending from a proximal end to a distal end;

a first electrode having a first lead body and an active fixation portion, said main lead body having a first recess therein housing the first electrode, the first electrode and the first lead body capable of moving between a first recessed position within said first recess and a second extended position outside the first recess so that the active fixation portion of the first electrode is adapted to attach to a wall of the heart, wherein the first electrode is positionable in the first recessed position when the lead is being surgically inserted;

a second electrode associated with the main lead body, the first electrode adapted to be housed with a first chamber of the heart and the second electrode adapted to be housed within a second chamber in the heart, said main lead body having a second recess therein housing the second electrode, the second electrode capable of moving between a first recessed position within said second recess and a second extended position outside the second recess so that the second electrode is adapted to attach to the wall of the heart; and wherein the main lead body includes a lubricant within the recess.

29. The system of claim 28, wherein the first electrode is positionable in a first position within the recess when the lead is being surgically inserted.

30. The system of claim 28, wherein the first electrode is positionable in a second position outside of the recess, the position of the electrode controllable from the proximal end of the main lead body.

* * * * *